(12) United States Patent
Boylan et al.

(10) Patent No.: US 11,065,131 B2
(45) Date of Patent: Jul. 20, 2021

(54) INTERBODY FUSION SYSTEM AND METHODS

(71) Applicant: Spineology Inc., St. Paul, MN (US)

(72) Inventors: Clint Boylan, Minneapolis, MN (US); Kyle Wolff, Cottage Grove, MN (US); Garrett Ganske, Lino Lakes, MN (US); Todd Bjork, Hudson, WI (US); Dan Mcphillips, Andover, MN (US); Michael Wang, Miami, FL (US)

(73) Assignee: Spineology Inc., St. Paul, MN (US)

( * ) Notice: Subject to any disclaimer, the term of this patent is extended or adjusted under 35 U.S.C. 154(b) by 0 days.

(21) Appl. No.: 16/140,499

(22) Filed: Sep. 24, 2018

(65) Prior Publication Data
US 2019/0091038 A1    Mar. 28, 2019

Related U.S. Application Data

(60) Provisional application No. 62/562,345, filed on Sep. 22, 2017.

(51) Int. Cl.
| | | |
|---|---|---|
| *A61F 2/46* | (2006.01) | |
| *A61B 17/02* | (2006.01) | |
| *A61B 1/00* | (2006.01) | |
| *A61B 90/50* | (2016.01) | |
| *A61F 2/44* | (2006.01) | |
| *A61B 1/32* | (2006.01) | |
| *A61B 90/57* | (2016.01) | |
| *A61B 90/00* | (2016.01) | |
| *A61B 17/00* | (2006.01) | |
| *A61B 90/30* | (2016.01) | |

(52) U.S. Cl.
CPC ........ *A61F 2/4611* (2013.01); *A61B 1/00154* (2013.01); *A61B 17/0218* (2013.01); *A61B 90/57* (2016.02); *A61B 1/32* (2013.01); *A61B 2017/00261* (2013.01); *A61B 2017/0256* (2013.01); *A61B 2090/306* (2016.02); *A61B 2090/376* (2016.02); *A61F 2/4455* (2013.01); *A61F 2002/4625* (2013.01)

(58) Field of Classification Search
CPC . A61B 17/02; A61B 17/0206; A61B 17/0218; A61B 2017/0256; A61B 2017/0268
See application file for complete search history.

(56) References Cited

U.S. PATENT DOCUMENTS

| | | | | |
|---|---|---|---|---|
| 2008/0221394 A1* | 9/2008 | Melkent | ............... | A61B 17/025 600/201 |
| 2013/0289354 A1* | 10/2013 | Ainsworth | ......... | A61B 17/0206 600/204 |
| 2014/0303666 A1* | 10/2014 | Heiman | ............... | A61B 17/025 606/198 |

\* cited by examiner

*Primary Examiner* — Matthew J Lawson
*Assistant Examiner* — Lisa Nguyen
(74) *Attorney, Agent, or Firm* — Skaar Ulbrich Macari, P.A.

(57) ABSTRACT

A portal system for intervertebral surgical fusion procedures includes a longitudinally elongated hollow tubular body comprising a first wall, a second wall opposing the first and a third wall spanning from a first edge of the first wall to a first edge of the second wall. A channel is defined longitudinally through at least one of the first, second and third end walls. The fourth wall of the body is at least partially open or can be completely enclosed.

7 Claims, 6 Drawing Sheets

INTERBODY FUSION SYSTEM AND METHODS

PRIORITY

This application claims the benefit of U.S. Provisional Application Ser. No. 62/562,345, filed on Sep. 22, 2017, which is hereby incorporated herein by reference in its entirety.

FIELD

The present invention generally relates to devices used in orthopedic surgeries, and more particularly to instruments, implants, tools and methods used for spinal surgical procedures such as interbody fusion procedures.

BACKGROUND

In surgical procedures it is desirable to provide convenient and access to the patient's anatomy for performing the procedure and for delivering implants, instruments and the like while minimizing trauma to the patient. There is an ongoing need to provide instruments, implants, tools and methods used for spinal surgical procedures such as interbody fusion procedures that improve upon the conventional art as discussed herein.

SUMMARY

The disclosed Interbody Fusion System incorporates the essential functional requirements taken to be industry standard for the lateral interbody vertebral fusion procedure, but dramatically reduces necessary exposure area and improves fluoroscopic visualization of the disc site.

Unlike all other lateral retractors on the market, the disclosed tubular portal requires no actuation to perform the discectomy or to implant the interbody spacer. The portal includes features to allow the user to insert various fixation elements (e.g. fixation pins, intradiscal shims) or lighting elements through multiple universal ports. The tubular portal's oval shape is unique, allowing the user to gain additional access above/below the disc site or along the plane of the disc.

In transpsoas lateral fusion surgery, the disc site is accessed by transecting the psoas muscle. The lateral lumbar plexus runs directly through the psoas muscle in the lower lumbar spine. Retracting the psoas muscle (and retraction in lateral surgery in general) has been linked to immediate post-op issues (e.g. thigh and groin numbness, pain, dysthesia, thigh weakness). By significantly reducing the overall amount of retraction (in this case, as much as a 50% reduction in overall retraction amount), it may be possible to reduce the severity and/or frequency of these post-op issues.

The disclosure includes a portal system for intervertebral surgical fusion procedures that includes a longitudinally elongated hollow tubular body comprising a first wall, a second wall opposing the first and a third wall spanning from a first edge of the first wall to a first edge of the second wall. A channel is defined longitudinally through at least one of the first, second and third end walls.

The body can define an opening extending along at least a portion of a fourth longitudinal side thereof, the fourth longitudinal side being located opposite the third wall and spanning between a second edge of the first wall and a second edge of the second wall. The fourth wall located opposite the third wall and spanning between a second edge of the first wall and a second edge of the second wall can also be solid.

The channel can be a rectangular slot when viewed in a lateral cross-section. The channel can include an opening to the hollow interior of the body. The channel can also be circular bore when viewed in a lateral cross-section, or can have another suitable shape for receiving tools, fasteners or instruments.

The distal end of the body can be angled with respect to a longitudinal axis of the body.

The body, when viewed in a lateral cross-section, is a rectangle with rounded corners.

A clamp securable to the body is also disclosed herein.

The disclosure further includes surgical methods as will be discussed below.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims. For illustrative purposes, cross-hatching, dashing or shading in the figures is provided to demonstrate sealed portions and/or integrated regions or devices for the package.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, dimensional relationships among individual elements in the attached drawings are illustrated only for ease of understanding, but not to limit the actual scale unless specifically claimed as such.

The instruments, implants, tools and methods of the present invention include a portal system 10 which greatly reduces the disruption to the patient's anatomy as compared to traditional retraction systems, a discectomy systems, and implants. An example implant that can be used in conjunction with the portal system is disclosed in U.S. Pat. No. 9,925,058 B2, which is fully incorporated herein by reference. Other types of implants can also be used with the present portal system. The portal system is particularly adapted for use in spinal surgical procedures, and particularly interbody vertebral fusion procedures. However, the portal system can be adapted to other procedures as well.

The portal system 10 components, methods and implant are configured and selected to minimize retraction of the patient's neural structures and soft tissue to reduce the post-operative complications commonly associated with the lateral decubitus approach. Traditional retractor systems require an access opening of about 22 mm superior to inferior retraction and about 33 mm anterior to posterior retraction to place a 22 mm width interbody implant.

In certain embodiments, the portal system 10, methods and implant allow for a greatly reduced access opening of about 20 mm superior to inferior and about 18 mm anterior to posterior to accommodate placement of an equivalently sized implant.

Figure 1A:
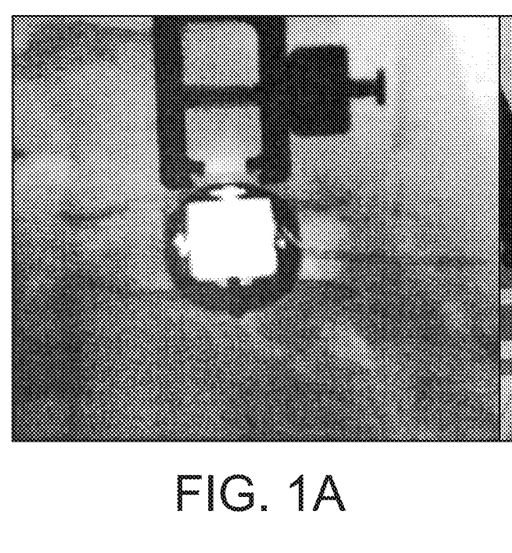
FIG. 1A depicts an image of a portal in accordance with certain embodiments of the invention.
Figure 1B:
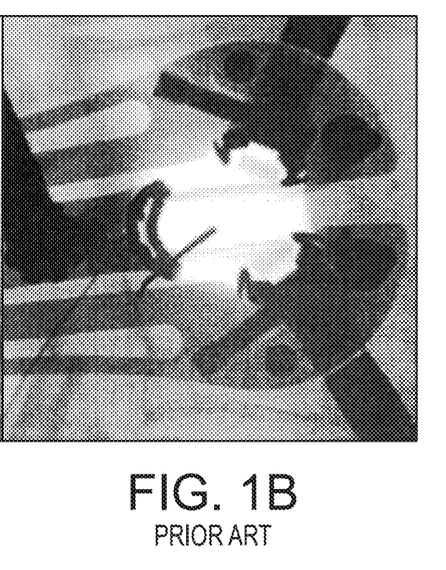
FIG. 1B depicts an image of a conventional retractor.

When implanting a 26 mm wide implant, traditional retractor systems, such as those shown in FIG. 1B, require about 24 mm of superior to inferior retraction and about 39 mm of anterior to posterior retraction. In contrast, certain embodiments of the present portal system, methods and implant only require an access of 20 mm superior to inferior and 18 mm anterior to posterior to accommodate placement of an equivalently sized implant. Thus, the present invention, such as shown in FIG. 1A, can reduce the amount of retraction by up to 47% when a 22 mm width implant is used and up to 58% when a 26 mm implant is used, as compared to a conventional retractor.

Figure 2A:
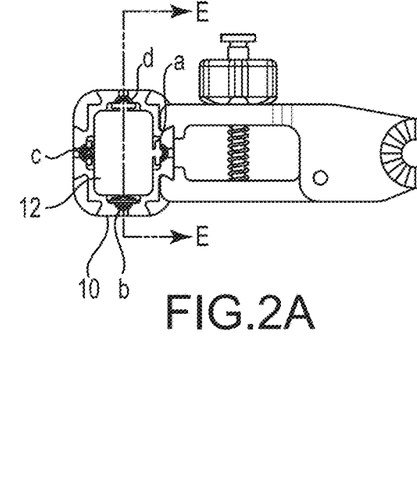
FIG. 2A is a top view of a tubular portal in accordance with certain embodiments of the invention.
Figure 2B:
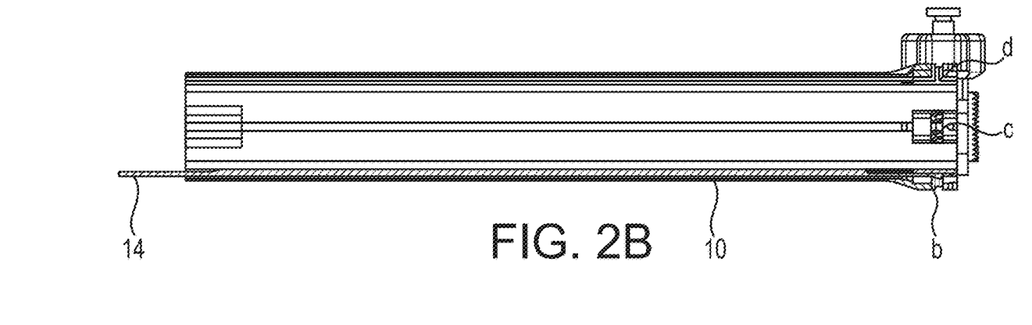
FIG. 2B is a cross-sectional side view of the tubular portal of FIG. 2A, taken along line E-E thereof, in accordance with certain embodiments of the invention.
Figure 2C:
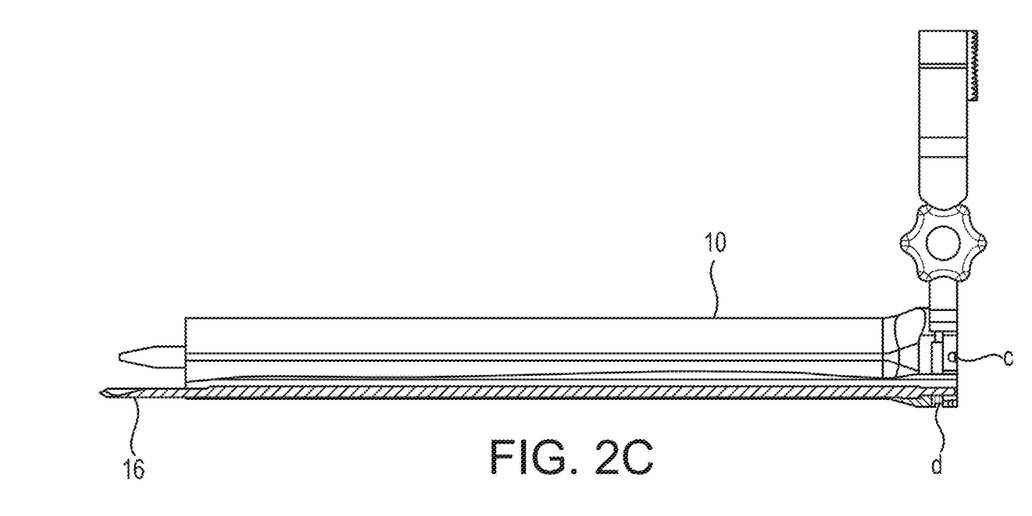
FIG. 2C is a side view of the tubular portal of FIG. 2A in accordance with certain embodiments of the invention.

One example embodiment of the portal system is shown in FIGS. 2A-2C. The tubular portal 10 may be configured as an enclosed tube with a generally rectangular cross-sectional shape. The corners of the rectangle can be rounded as shown in FIG. 2A. Other shapes, including but limited to oval and square are contemplated. Portal 10 may be rotated after placement to accommodate visualization according to physician preference. The shape of portal 10 minimizes medial-lateral retraction and is in line with the muscle fibers thus there less pulling on the psoas muscle.

Portal 10 can include channels, grooves, T-slots, indentations or other attachment features defined on or in one or more of the walls 12 that form the tubular body. In FIGS. 2A-2C, there is a channel a, b, c and d defined in each of the four walls 112 that define the tubular body. Each channel can define a narrower opening into the interior of the body and a wider internal width inside of the wall.

The channels a, b, c, d are configured to receive accessory tools such as shims 14, pins or screws 16 that can be used to secure portal 10 to the patient's vertebral bone. Other tools such as light cables, endoscopic cameras or any other desired tool can be provided to one or more of the channels to aid in the surgeon in the surgical procedure. These accessory tools may be placed in any of slots a, b, c, d at any point during the procedure. Each slot can be provided with a different tool or multiples of the same tool.

Light fibers may be positioned at any length along any of the slots a, b, c, d. Light fibers may include markings that correspond to a particular portal longitudinal length. Shims 14 may be placed in any of the slots a, b, c, d to aid in holding tissue safely out of the operative space. Shims 14 may include a spring-loaded portion which snaps under a tab on portal 10. A shim puller may be used to disengage the snap to pull shim out.

Fixation pins and/or screws 16 may be placed in any of the slots a, b, c, d, to secure portal 10 to a vertebral body. Screws 16 may be manually secured or by using a powered screw driver. Screw/pin 16 may have a threaded and/or textured end to grip bone thus maintaining position of portal 10. Because screw/pin 16 is within portal 10, there is no need to retract open further.

In an alternative embodiment, channels or a cannulated hole may be bored within portal 10 wall sections 12. Accessory tools may then be placed through the bored hole. In such an embodiment, a light fiber may be placed down portal tube 10 directly. The interior of portal 10 may be black to enhance visualization and lighting. Portal 10 may include an exposed, uncoated distal end to allow neuro-monitoring. The distal end of portal tube 10 may be angled or otherwise contoured to more closely conform to the shape of the vertebral body. Portal tube 10 may be radiolucent.

Figures 3A, 3B:
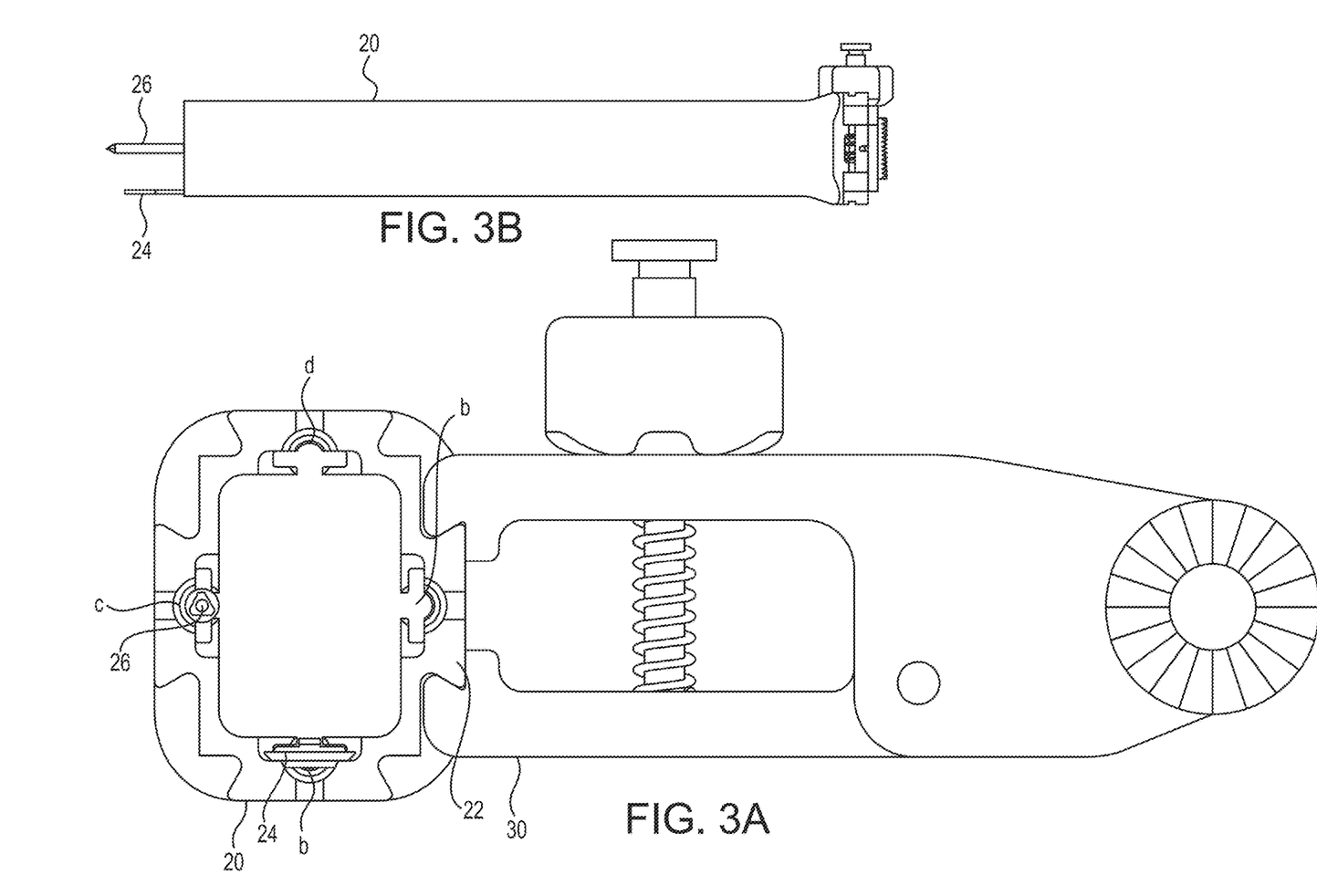
FIG. 3A is a top view of a tubular portal in accordance with certain embodiments of the invention.
FIG. 3B is a side view of the tubular portal of FIG. 3A in accordance with certain embodiments of the invention.

FIGS. 3A and 3B depict another embodiment where to portal 20 is provided with a clamp mechanism 30. Portal 20 may be configured similar the portal 10 of FIGS. 2A-2C.

Clamp 30 may attach to a table arm, support member, framework or other mechanism on or in the operating room. Clamp 30 on one end attaches to dovetail portion 22 defined in an outer surface of a wall of the portal 20.

FIG. 3A illustrates the proximal or top openings of the slots a, b, c, d used for the insertion of accessory tools as discussed herein. A shim 24 is shown placed in slot b's opening and screw 26 is shown placed in slot c's opening. Both of these items or tools protrude distally below the portal 20 as shown in FIG. 3B.

Figure 4A:
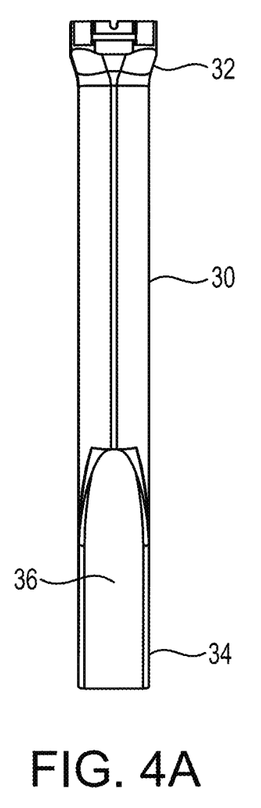
FIG. 4A is a front view of a tubular portal in accordance with certain embodiments of the invention.
Figure 4B:
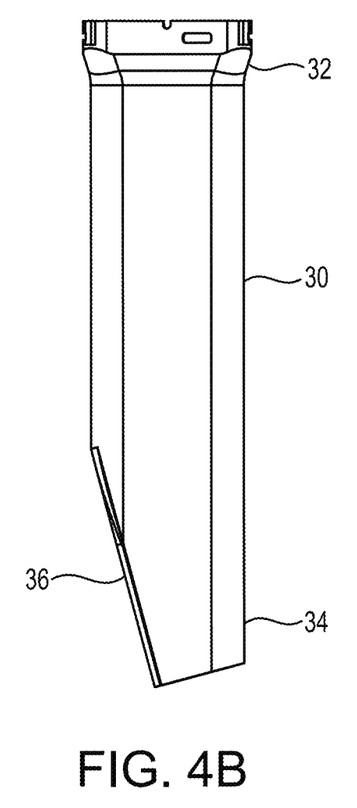
FIG. 4B is a side view of the tubular portal of FIG. 4A in accordance with certain embodiments of the invention.
Figure 4C:
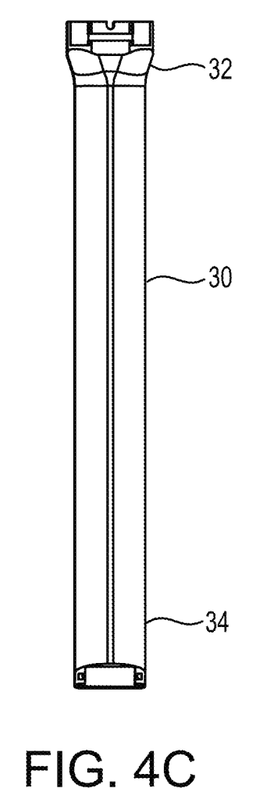
FIG. 4C is a rear view of the tubular portal of FIG. 4A in accordance with certain embodiments of the invention.

FIGS. 4A-C depict a further alternative embodiment of the portal system. The portal 30 may be include any or all of the features of portals 10 and 20. In addition, the tubular body of portal 30 may be configured to have a tapered body width, such that the proximal portion 32 of portal 30 may be wider than the distal portion 34. The wider proximal portion 32 allows the user to angle instruments back and forth and side to side as desired during the surgical procedure while maintaining the small access at distal portion 34. Distal portion 34 may include an opening 36 to allow free movement of instruments, such as discectomy instruments.

Figure 5A:
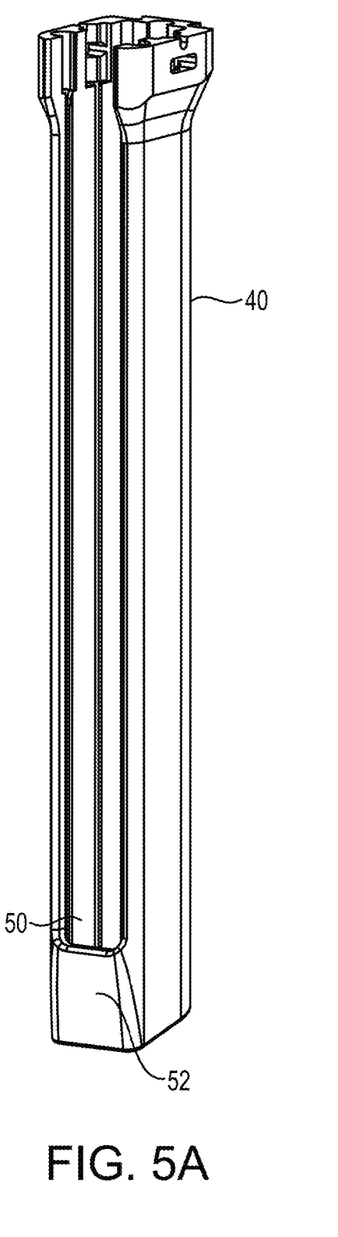
FIG. 5A is a perspective view of a portal in accordance with certain embodiments of the invention.
Figures 5B, 5C:
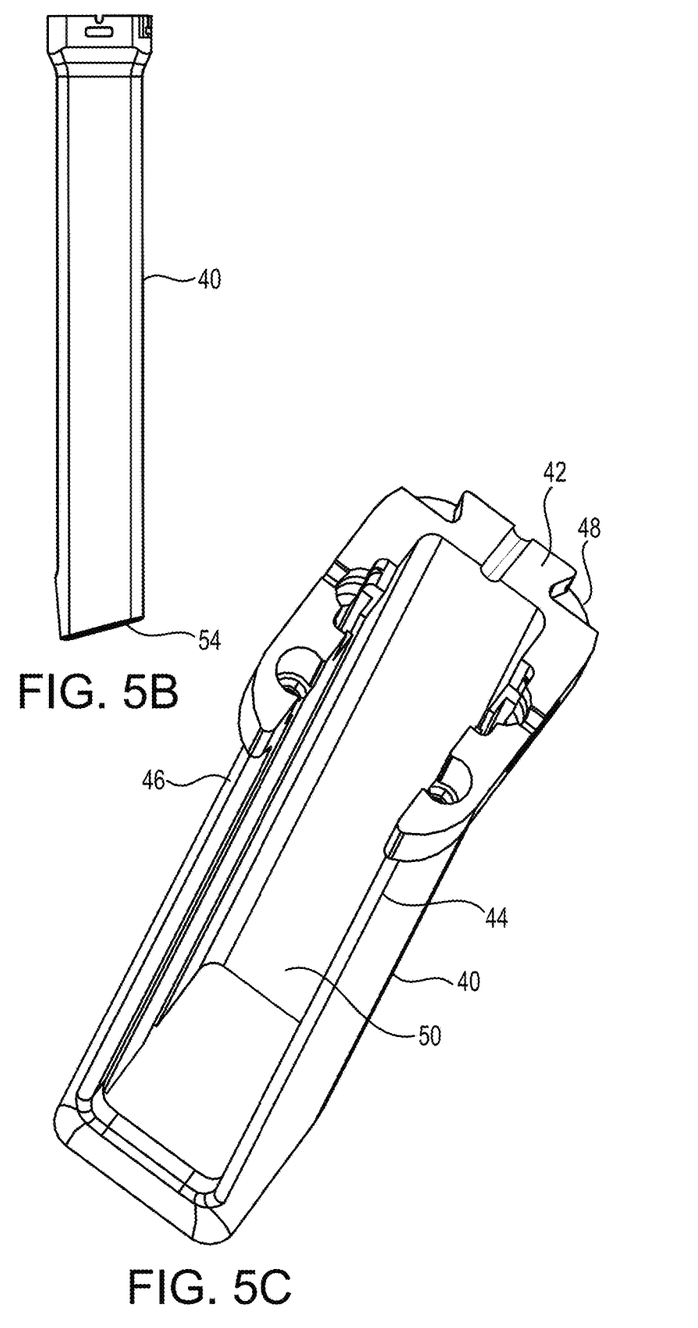
FIG. 5B is a side view of the portal of FIG. 5A in accordance with certain embodiments of the invention.
FIG. 5C is another perspective view of the portal of FIG. 5A in accordance with certain embodiments of the invention.

FIGS. 5A-5C depict yet another embodiment of the portal system. The body of portal 40 comprises three walls: two lateral walls 42 and 44 and a superior wall 46. In place of an inferior wall, the body defines an opening 50. Portal 40 may include all the features of portals 10 and 20. Opening 50 allows for free movement of surgical instruments while maintaining a small surgical access opening. This embodiment may be particularly useful when accessing the L4-L5 vertebral segment. In use, opening 50 faces the patient's ileac crest to allow for instrumentation access. Portal 40 may include an angled distal end 54 to reach under the patient's ileac crest.

As shown in FIG. 5A, a portion of the distal end 52 can be provided with a partial fourth wall to structurally support the other three walls.

A sheath, cover, shim or other flexible or disposable component can be used to close over opening 50, thereby effectively making an enclosing fourth wall. Portal 40 may alternatively include a hinged door, hatch or other removable component placed in the opening 50 above the distal end wall portion 52 to create an enclosing fourth wall.

Figure 6A:
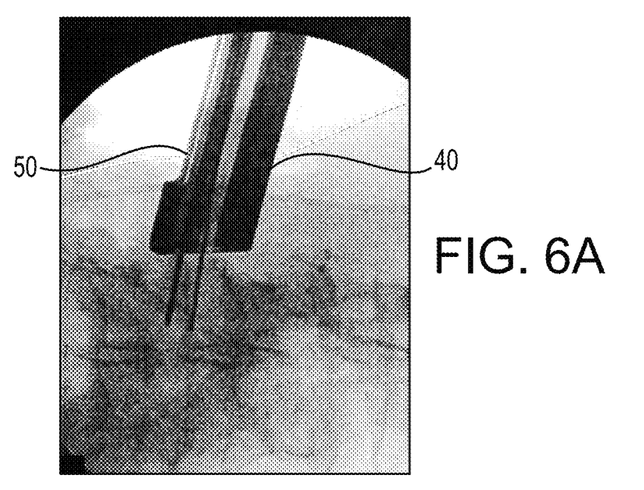
FIGS. 6A-6C are images of portals in use in accordance with certain embodiments of the invention.

In use, as is shown in FIG. 6A, a surgical method according to an example embodiment of the present invention may include: advancing a dilator into a disc space; placing a clamp over angled portal tube dovetail on the posterior side; tightening the thumbscrew on the clamp to affix it to portal tube 40; passing portal tube 40 over the dilators, ensuring the open side 50 of the angled portal tube 40 is facing the foot of the patient (iliac crest), and advancing the assembly until the distal end of the portal tube 40 contacts the disc space.

Figure 6B:
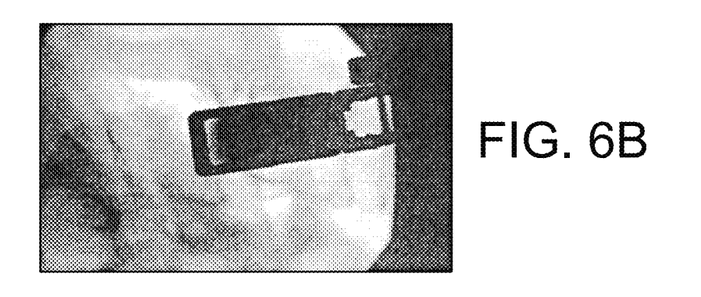

FIG. 6B shows the steps of confirming portal tube 40 position and trajectory using lateral and AP images and attaching a table arm to portal tube 40.

Figure 6C:
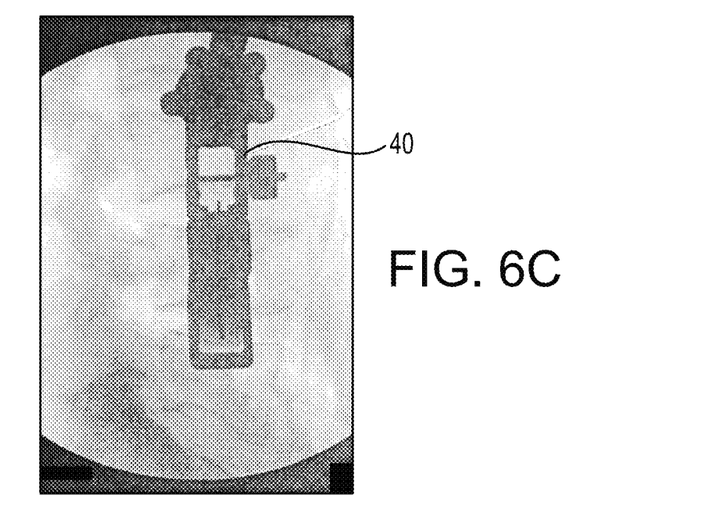

FIG. 6C depicts the steps of placing a fixation pin in one or two of the portal tube 40 channels a, b, c, d and advancing the pin into the vertebral body to secure portal tube 40 to the vertebral body. Then the dilators and guide wire may be removed, leaving portal tube 40 in place.

A light cable may then be passed down one of the remaining portal tube channels until the line corresponding to the portal tube length used is reached. The light cable may be bent at the selected line. If desired, a shim may be placed into the posterior channel of the portal tube 40 and a shim inserter may be used to advance the shim until fully seated.

In yet another embodiment, in anterior surgery, safe retraction of the great vessels requires ligation and dissection of small segmental vessels in order to mobilize the great vessels safely, and even when done properly they may not be adequately mobile to retract sufficiently to place a device. Additionally, in lateral surgery, manipulation and prolonged retraction of the psoas muscle and the nerves contained therein can be a source of post-operative pain and functional loss.

The small size of the distal end of the portal tube 40 affords access to the spine at a location on the patient's left anterior oblique position between the great vessels and left psoas with minimal anatomic manipulation as this location is typically devoid of these anatomical structures. Additionally, portal tube 40 affords the surgeon the ability to temporarily move the surgical instruments into a position that is not co-linear with tube 40 in order to affect improved access to the disc for purposes of performing a thorough discectomy or implant placement.

In radical Discectomies, the discectomy instruments facilitate a broad, anterior lumbar interbody fusion (ALIF) sized discectomy through a much smaller minimally invasive surgical (MIS) access opening. Steps in the discectomy procedure through portal tubes according to an embodiment of the present invention may include:

Standard System Discectomy

1. Straight and angled Cobbs are used to remove cartilage from the central portion of the superior and inferior endplates;
2. Box cutters are used to capture and remove large fragments of disc material from the central portion of the disc space;
3. Pituitaries are used to remove loose disc material from the central portion of the disc space;
4. Straight rake or curettes are used to further remove cartilage from the central portion of the endplates;
5. Right rake or right curette is used to removed cartilage and disc material from the anterior quadrant of the superior endplate;
6. Left rake or left curette is used to removed cartilage and disc material from the anterior quadrant of the inferior endplate;
7. Right rake or right curette is used to removed cartilage and disc material from the posterior quadrant of the inferior endplate;
8. Left rake or left curette is used to removed cartilage and disc material from the posterior quadrant of the superior endplate;
9. Pituitaries are used to remove any lose disc material form the disc space; and
10. Dissecting Cobb is used to release contralateral annulus.

Angled Portal Tube System Discectomy (Specific to L4-L5)

1. L5 straight Cobb and L5 reverse angle Cobb are used to remove cartilage from the central portion of the L5 endplate;
2. L4 straight Cobb and L4 angled Cobb are used to remove cartilage from the central portion of the L4 endplate;
3. Curved pituitaries are used to remove loose disc material from the central portion of the disc space;
4. L4 straight rake is used to further remove cartilage from the central portion of the L4 endplate;
5. L5 straight rake is used to further remove cartilage from the central portion of the L5 endplate;
6. L4 angled rake is used to further remove cartilage from the anterior quadrant of the L4 endplate;
7. L5 angled rake is used to further remove cartilage from the anterior quadrant of the L5 endplate;
8. L4 angled rake is used to further remove cartilage from the posterior quadrant of the L4 endplate;
9. L5 angled rake is used to further remove cartilage from the posterior quadrant of the L5 endplate; and
10. L5 straight Cobb and L4 straight Cobb are used to release contralateral annulus.

In further embodiments, an intervertebral implant that includes at least a portion of expandable mesh (for example, U.S. Pat. No. 9,925,058 B2) is implanted in an unexpanded state to accommodate the small access opening created by the portal tube. The mesh component of the implant is configured to be filled with bone graft in-situ and expand to create a large, endplate conforming, load-sharing graft pack designed to facilitate broad endplate contact, support and fusion. The mesh portion of the implant expands in superior/inferior and anterior/posterior planes. A spacer portion (or portions) of the implant, which may be formed of PEEK, is placed on the apophysis to provide mechanical support. The implant resists subsidence to help maintain spinal correction.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A portal system for intervertebral surgical fusion procedures, comprising:
    a longitudinally elongated hollow body comprising a first wall, a second wall opposing the first, a third wall spanning from a first edge of the first wall to a first edge of the second wall and a fourth longitudinal side being located opposite the third wall and spanning between the second edge of the first wall and the second edge of the second wall; and
    a channel defined longitudinally through at least one of the first, second and third walls,
    wherein the fourth side defines an opening that extends from a proximal end of the longitudinally elongated hollow body towards a distal end of the longitudinally elongated hollow body for at least a majority of a longitudinal length of the longitudinally elongated hollow body, and
    wherein the fourth side further comprises a solid fourth wall portion located adjacent to the distal end, opposite the third wall, and spanning between a second edge of the first wall and a second edge of the second wall.

2. The portal system of claim 1, wherein the channel is a rectangular slot when viewed in a lateral cross-section.

3. The portal system of claim 2, wherein the channel includes an opening to the hollow interior of the body.

4. The portal system of claim 1, wherein the channel is a circular bore when viewed in a lateral cross-section.

5. The portal system of claim 1, wherein the body, when viewed in a lateral cross-section, is a rectangle with rounded corners.

6. The portal system of claim 1, further including a clamp securable to the body.

7. The portal system of claim 1, wherein the distal end of the body defines an opening that is larger than an opening defined in the proximal end of the body.

* * * * *